US010337971B2

(12) United States Patent
Gustafson

(10) Patent No.: US 10,337,971 B2
(45) Date of Patent: Jul. 2, 2019

(54) CONDITION-BASED MONITORING FOR MATERIALS IN WELLBORE APPLICATIONS

(71) Applicant: Hydril USA Distribution, LLC, Houston, TX (US)

(72) Inventor: Ryan Cheaney Gustafson, Houston, TX (US)

(73) Assignee: Hydril USA Distribution, LLC, Houston, TX (US)

( * ) Notice: Subject to any disclaimer, the term of this patent is extended or adjusted under 35 U.S.C. 154(b) by 176 days.

(21) Appl. No.: 15/011,153

(22) Filed: Jan. 29, 2016

(65) Prior Publication Data

US 2016/0223447 A1 Aug. 4, 2016

Related U.S. Application Data

(60) Provisional application No. 62/110,346, filed on Jan. 30, 2015.

(51) Int. Cl.
*G01N 3/56* (2006.01)
*E21B 41/00* (2006.01)
*G01N 17/04* (2006.01)
*E21B 33/06* (2006.01)
*E21B 47/06* (2012.01)

(52) U.S. Cl.
CPC .............. *G01N 3/56* (2013.01); *E21B 33/06* (2013.01); *E21B 41/00* (2013.01); *E21B 47/06* (2013.01); *E21B 47/065* (2013.01); *G01N 17/04* (2013.01); *G01N 2203/0244* (2013.01)

(58) Field of Classification Search
None
See application file for complete search history.

(56) References Cited

U.S. PATENT DOCUMENTS 3,364,737 A 1/1968 Comes
3,451,475 A * 6/1969 Price .................... E21B 49/001
166/319

(Continued)

FOREIGN PATENT DOCUMENTS

CA 1172051 8/1984
WO 2008009957 A1 1/2008

OTHER PUBLICATIONS

PCT Search Report and Written Opinion issued in connection with Corresponding Application No. PCT/US2016/015694 dated Apr. 7, 2016.

*Primary Examiner* — Jill E Culler
(74) *Attorney, Agent, or Firm* — Hogan Lovells US LLP

(57) ABSTRACT

A method for analyzing material wear in a hydrocarbon production environment is disclosed. The method includes the steps of preparing a sample of material to be disposed proximate the hydrocarbon production environment; selecting a placement location for the sample of material, wherein the placement location is in fluid communication with a fluid flow for which the impact of the fluid flow on the sample of material is to be tested; disposing the sample of material in the placement location for a pre-determined amount of time; allowing the sample of material to be exposed to the fluid flow; retrieving the sample of material from the placement location after the pre-determined amount of time has passed; and analyzing the sample of material for wear caused by the hydrocarbon production environment.

11 Claims, 7 Drawing Sheets

(56) References Cited

U.S. PATENT DOCUMENTS

| | | | |
|---|---|---|---|
| 4,488,578 A | 12/1984 | Tseung et al. | |
| 4,553,591 A * | 11/1985 | Mitchell | E21B 33/03 166/86.2 |
| 4,685,521 A * | 8/1987 | Raulins | E21B 29/04 166/341 |
| 4,791,822 A | 12/1988 | Penny | |
| 5,522,251 A * | 6/1996 | Scott | G01N 3/56 434/365 |
| 6,937,030 B2 | 8/2005 | Liney et al. | |
| 7,062,960 B2 | 6/2006 | Couren et al. | |
| 7,660,197 B2 * | 2/2010 | Barolak | E21B 47/0006 181/105 |
| 8,430,168 B2 | 4/2013 | Goodall et al. | |
| 2013/0160525 A1 | 6/2013 | Sweeney | |

\* cited by examiner

CONDITION-BASED MONITORING FOR MATERIALS IN WELLBORE APPLICATIONS

RELATED APPLICATIONS

This application is a non-provisional application claiming priority to U.S. Provisional Application No. 62/110,346, filed Jan. 30, 2015, which is hereby incorporated herein by reference in its entirety.

BACKGROUND

1. Field of Invention

This disclosure relates in general to oil and gas equipment, and to testing materials used in oil and gas equipment for wear. In particular, the disclosure provides systems and methods that accurately assess wear on materials used in oil and gas equipment under varying environmental conditions.

2. Related Technology

The American Petroleum Institute requires fatigue analysis on materials exposed to certain environmental conditions when the materials are to be used in oil and gas operations. These operations can include high pressure high temperature (HPHT) operations and subsea operations. However, environmental conditions vary from well to well, and no single analysis can be used to determine the expected lifespan of a given piece of oil and gas equipment. Laboratory scale tests cannot accurately mimic the environment found in harsh hydrocarbon production environments, such as a subsea wellbore, and cannot accurately gauge the expected lifespan of a given piece of oil and gas equipment when exposed to such harsh environments.

SUMMARY

Systems and methods for accurately assessing wear on materials in wellbore environments, including subsea applications, are disclosed. Materials can be installed and exposed to wellbore fluids in racks within one or more unused blowout preventer (BOP) outlets. The sample size of material can vary to assess equipment design life. Material degradation can be measured over time for the particular environmental conditions affecting a sample. For metallic samples, such materials can be connected to wellbore materials that are connected to a system's cathode protection system. For elastomeric material samples, such samples can be tested against manufacturing material properties and can be analyzed in the wellbore environment to test equipment performance and to establish better life and service recommendations, as well as compound improvements.

Subsea systems can be protected cathodically by using anodes rated for the environment. Anodes are sized in accordance with industry specifications based on the material grades, surface preparation, surface areas, as well as other factors. The sacrificial anodes are mounted in various locations on a BOP and connected so that they limit degradation in the subsea equipment for the expected design life.

Therefore, disclosed herein is a method for analyzing material wear in a hydrocarbon production environment. The method includes the steps of: preparing a sample of material to be disposed proximate the hydrocarbon production environment; selecting a placement location for the sample of material, wherein the placement location is in fluid communication with a fluid flow for which the impact of the fluid flow on the sample of material is to be tested; and disposing the sample of material in the placement location for a pre-determined amount of time. The method further includes the steps of allowing the sample of material to be exposed to the fluid flow; retrieving the sample of material from the placement location after the pre-determined amount of time has passed; and analyzing the sample of material for wear caused by the hydrocarbon production environment.

Additionally disclosed is a monitoring vessel for analyzing material wear in a hydrocarbon production environment. The vessel includes a retainer operable to hold a sample of material to be disposed proximate the hydrocarbon production environment; a fluid flow channel operable to allow a fluid flow through the retainer, for which the impact of the fluid flow on the sample of material is to be tested; and an end cap, wherein the end cap is operable to allow insertion of the sample of material into the retainer, and removal of the sample of material from the retainer.

BRIEF DESCRIPTION OF THE DRAWINGS

These and other features, aspects, and advantages of the present disclosure will become better understood with regard to the following descriptions, claims, and accompanying drawings. It is to be noted, however, that the drawings illustrate only several embodiments of the disclosure and are therefore not to be considered limiting of the disclosure's scope as it can admit to other equally effective embodiments.

DETAILED DESCRIPTION

Figure 1:
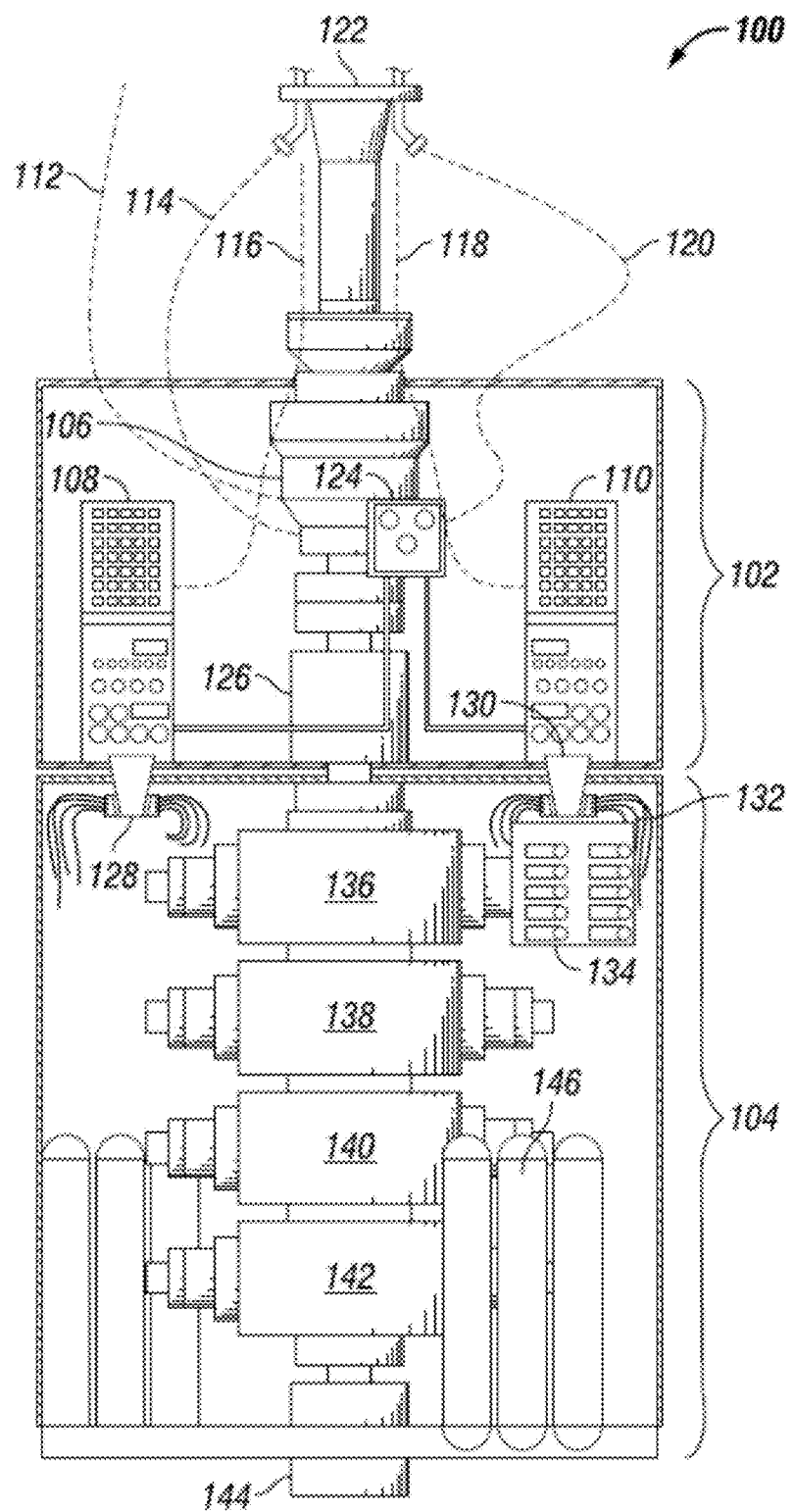
FIG. 1 is a representative system overview of a BOP stack.

So that the manner in which the features and advantages of the embodiments of systems and methods of condition-based monitoring for materials in wellbore applications, as well as others, which will become apparent, may be understood in more detail, a more particular description of the embodiments of the present disclosure briefly summarized previously may be had by reference to the embodiments thereof, which are illustrated in the appended drawings, which form a part of this specification. It is to be noted, however, that the drawings illustrate only various embodiments of the disclosure and are therefore not to be considered limiting of the present disclosure's scope, as it may include other effective embodiments as well.

The present technology relates to fatigue analysis and testing of materials used in oil drilling or production equipment. High pressure high temperature (HPHT) well control equipment is required by regulation to undergo fatigue analysis on materials exposed to the environmental conditions at and in the well. Currently, there are no destructive testing procedures available to monitor the material properties while exposed to the environment. The ability to carry out such destructive testing would allow a user to predict the life of the material, and the equipment made of the material, to better predict the life of the equipment, and to ensure that the equipment meets the design requirements in the actual operating service conditions instead of lab conditions.

Typically, testing of equipment and materials requires that a few conditions are submitted for a baseline analysis, but there is no condition-based monitoring during the service life of the equipment except for non-destructive testing (for pitting and cracks) and hardness testing. This can be problematic because, while equipment may see similar conditions throughout the life of the equipment at a particular well, drilling equipment typically moves from well to well during its life, and conditions at different wells may vary.

The present technology includes a procedure wherein material sampling vessels are installed in blowout preventers (BOPs), or other oilfield equipment, on site at different wells, and exposed to the well fluids, and also other fluids such as sea water and air, in and around the BOPs. Material can be introduced and removed on a time-based cycle program (e.g., yearly), and the material properties tested to confirm the material is within the design limits prescribed for the equipment. Records during the service conditions can record pressure and temperature cycles as well as fluid properties (mud type, seawater exposure, production fluid exposure with durations) and external loading (riser tension and bending moments) to be evaluated when comparing material compatibility (both metallic and elastomeric). Such a system is advantageous because it better predicts service life of the components under the actual field conditions instead of a lab analysis which cannot accurately simulate environmental conditions for drilling equipment when it is moved from well to well.

Referring first to FIG. 1, a representative system overview of a BOP stack is shown. In FIG. 1, a BOP stack 100 is pictured, which includes a lower marine riser package (LMRP) 102 and a lower stack (LS) 104. LMRP 102 includes an annular 106, a blue control pod 108, and a yellow control pod 110. A hotline 112, a blue conduit 114, and a yellow conduit 120 proceed downwardly from a riser 122 into LMRP 102 and through a conduit manifold 124 to control pods 108, 110. A blue power and communications line 116 and a yellow power and communications line 118 proceed to control pods 108, 110, respectively. An LMRP connector 126 connects LMRP 102 to LS 104. Hydraulically activated wedges 128 and 130 are disposed to suspend connectable hoses or pipes 132, which can be connected to shuttle panels, such as shuttle panel 134.

LS 104 can include shuttle panel 134, as well as a blind shear ram BOP 136, a casing shear ram BOP 138, a first pipe ram 140, and a second pipe ram 142. BOP stack 100 is disposed above a wellhead connection 144. LS 104 can further include optional stack-mounted accumulators 146 containing a necessary amount of hydraulic fluid to operate certain functions within BOP stack 100.

Figure 2A:
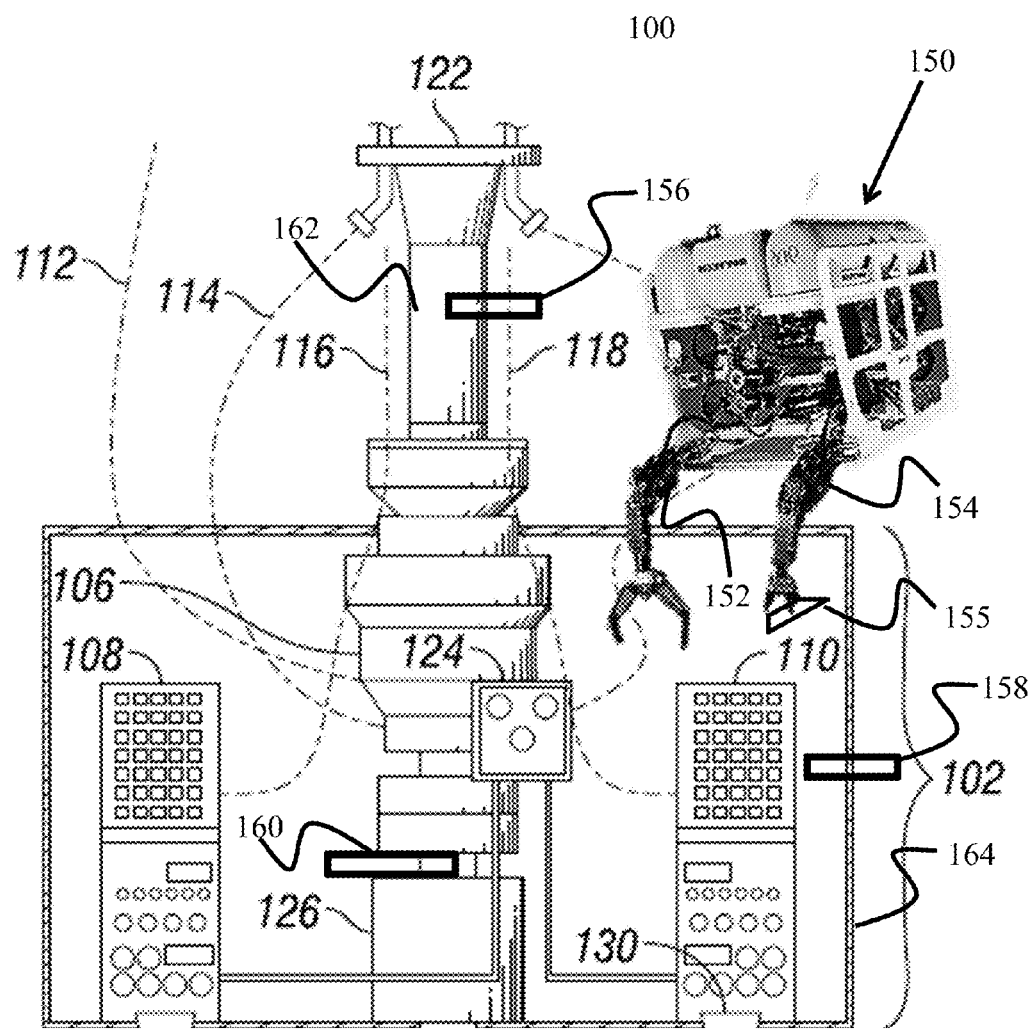
FIG. 2A is a schematic showing a remotely operated vehicle (ROV) accessing a lower marine riser package (LMRP) subsea.

Referring now to FIG. 2A, LMRP 102 from FIG. 1 is shown as being enlarged, and remotely operated vehicle (ROV) 150 is shown accessing LMRP 102. ROV 150 is controlled from the surface, and has access arms 152, 154. In FIG. 2A, LMRP 102 shows monitoring vessels 156, 158, and 160. Monitoring vessels 156, 160 are fluidly coupled to and in fluid communication with production line 162. Therefore, when drilling fluids and production fluids, such as for example drilling mud, brine, hydrocarbons, oil, natural gas, and condensates, are flowing through production line 162, such fluids also flow through monitoring vessels 156, 160. Monitoring vessel 158 is coupled to LMRP rack 164, and is in fluid communication with seawater surrounding BOP stack 100.

While monitoring vessels 156, 158, and 160 are shown mounted in certain positions on BOP stack 100, monitoring vessels could be mounted or located at any point on a BOP stack to assess environmental impacts on a material. Additionally, while monitoring vessels 156, 158, and 160 are shown being used in a subsea application, such monitoring vessels could be used in a land-based wellbore monitoring application in-situ, or in the ground. Monitoring vessels 156, 158, and 160 can represent existing unused outlets on a BOP stack, or can represent monitoring vessels specifically added to a BOP stack to assess environmental impact on materials. Such monitoring vessels can be integrally formed with BOP elements, such as for example production line 162, or monitoring vessels can be added after the installation of a BOP stack by an ROV, such as ROV 150.

ROV 150 with access arms 152, 154 can access monitoring vessels 156, 158, and 160 to insert material samples for the properties of the material samples to be assessed over time when exposed to the environmental conditions at the BOP stack 100. For example, a material sample 155 can be placed within monitoring vessel 160 by ROV 150 for monitoring in the presence of production fluid in production line 162. Additionally, ROV 150 can add and remove monitoring vessels, such as monitoring vessels 156, 158, and 160, to and from BOP stack 100. Monitoring vessels can be attached and removed from BOP stack 100 by any suitable means in the art including welding, bolting, and magnetic coupling. However, as noted, monitoring vessels can also be pre-existing unused outlets on a BOP stack integrally formed with existing elements on the BOP stack. After a material sample has been exposed to an environment for a suitable pre-determined amount of time, the material sample can be retrieved for analysis and testing in a laboratory.

In some embodiments, monitoring vessels are not ROV retrievable and would be mounted on or in BOP equipment, and when an LMRP and/or lower stack is retrieved to surface, then the samples could be removed and sent in for testing.

Figure 2B:
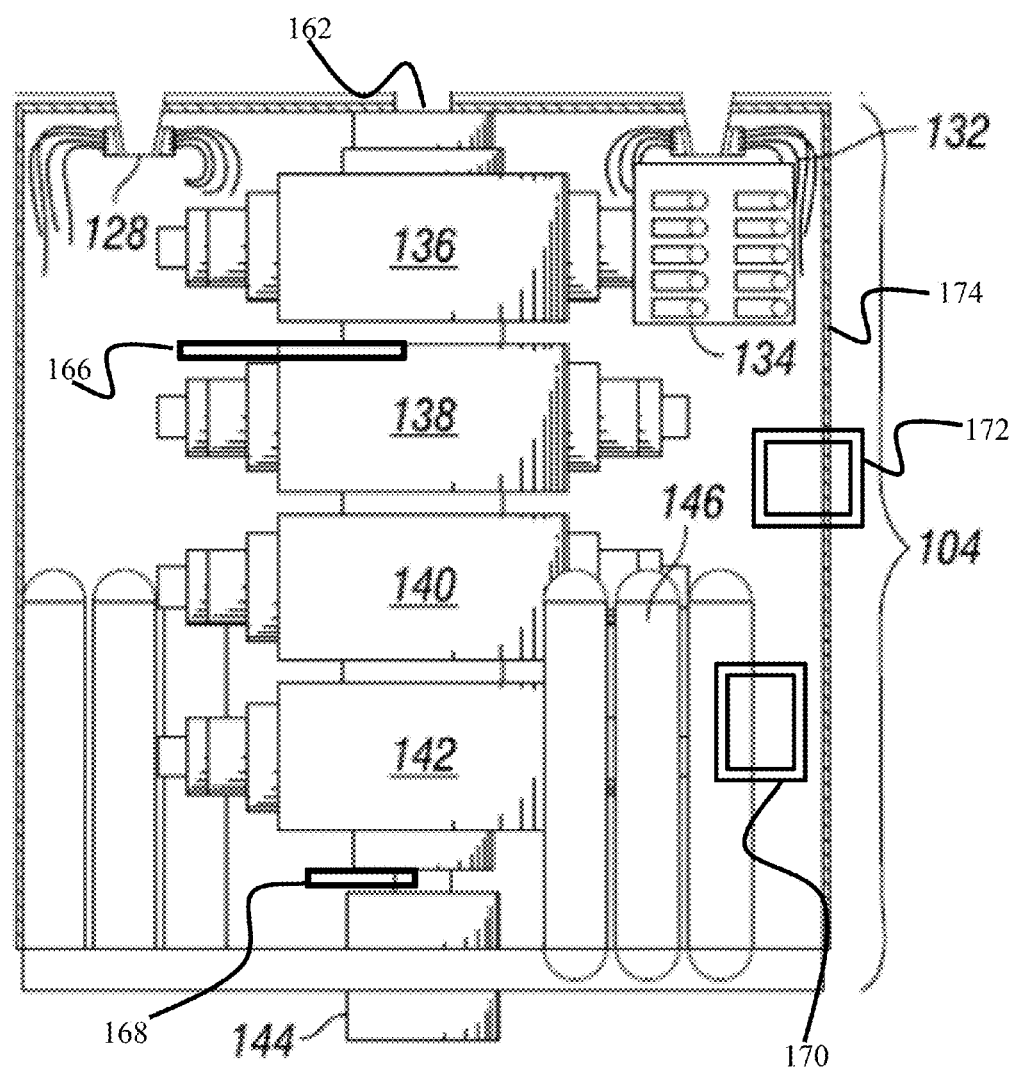
FIG. 2B is a schematic showing an enlarged view of the lower stack (LS) from FIG. 1.

Referring now to FIG. 2B, a schematic is provided showing an enlarged view of the lower stack (LS) from FIG. 1. Monitoring vessels 166, 168, 170, and 172 are disposed at particular locations on LS 104; however, in other embodiments monitoring vessels could be placed at other locations on LS 104. Monitoring vessel 166 is fluidly coupled to production line 162 through casing shear ram BOP 138; monitoring vessel 168 is fluidly coupled to production line 162 above wellhead connection 144; monitoring vessel 170 is fluidly coupled to stack-mounted accumulators 146; and monitoring vessel 172 is coupled to LS frame 174. When drilling fluids and production fluids, such as for example drilling mud, brine, hydrocarbons, oil, natural gas, and condensates, are flowing through production line 162, such fluids also flow through monitoring vessels 166, 168. A material sample in monitoring vessel 170 can be exposed to hydraulic fluid flow in stack-mounted accumulators 146. A material sample in monitoring vessel 172 can be exposed to seawater from the environment surrounding BOP stack 100.

Figure 3:
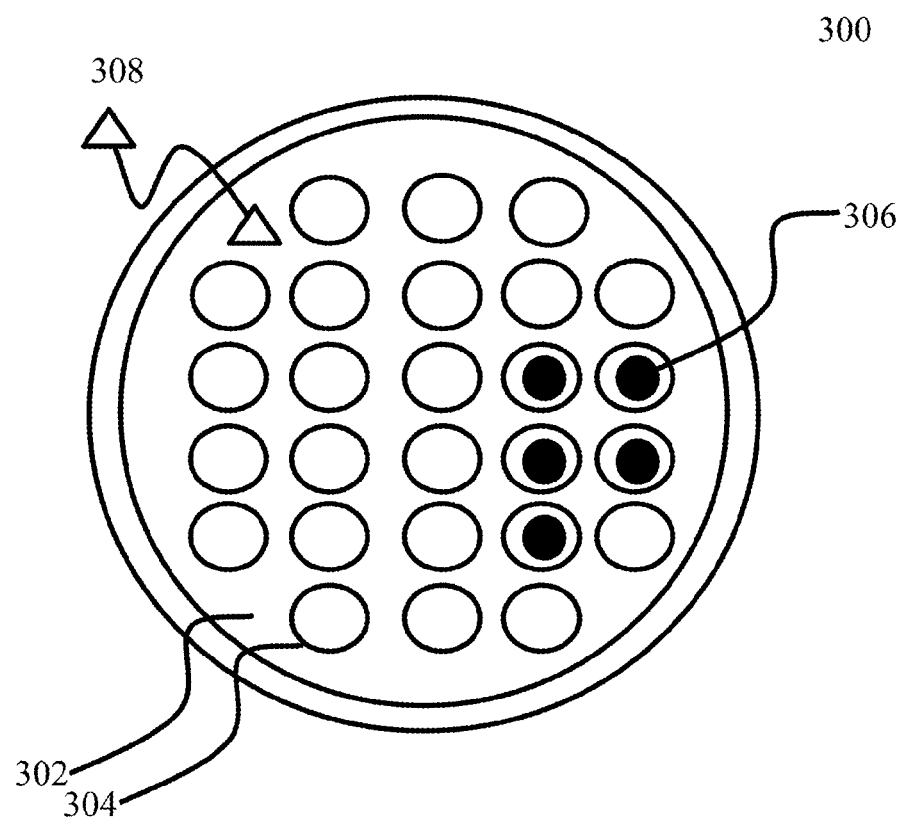
FIG. 3 is a cross-sectional schematic representation of a BOP outlet for sample monitoring.

Referring now to FIG. 3, a cross-sectional schematic representation of a BOP outlet for sample testing is provided. BOP outlet 300 serves as a monitoring vessel to assess wear on materials, similar to monitoring vessels 156, 158, 160, 166, 168, 170, and 172 shown in FIGS. 2A and 2B.

In some embodiments, a BOP outlet has a diameter of about 3.06 inches. In BOP outlet 300, a retainer 302 with sample compartments 304 holds sample materials 306. Sample materials 306 can include any material relevant to hydrocarbon recovery procedures, such as metals and elastomers, which require wear testing and exposure to a hydrocarbon recovery environment. In some embodiments, the material samples tested comprise materials that make up nearby oil and gas equipment, such as for example a BOP. BOP outlet 300 and/or sample materials 306 can be placed by an ROV. Sample materials 306 are exposed to fluids, such as hydrocarbon production fluids or seawater, when sample compartments 304 are fluidly coupled to a flow line or open to the surrounding fluid environment.

Sample materials, such as sample materials 306, can be recovered and tested for wear on an agreed upon timeline, such as annually or semi-annually. Lab testing, such as testing for material degradation, can be performed on relevant sample materials, including metals and elastomers, to provide an accurate estimate for the useful life of a material in a specific environment. In some embodiments, testing can be performed proximate a BOP outlet or sample retainer and proximate a hydrocarbon recovery environment. BOP outlet 300 includes a cathodic connection 308 for use with metal samples. In certain embodiments, a cathodic connection such as cathodic connection 308 would be required for use only with metallic samples, and not for use with elastomeric samples.

Subsea systems are typically protected cathodically by using anodes rated for the environment. Anodes are sized in accordance with industry specifications based on the material grades, surface preparation, surface areas as well as some other factors. The sacrificial anodes are mounted in various locations and connected so that they limit degradation in the subsea equipment for the expected design life.

Figure 4:
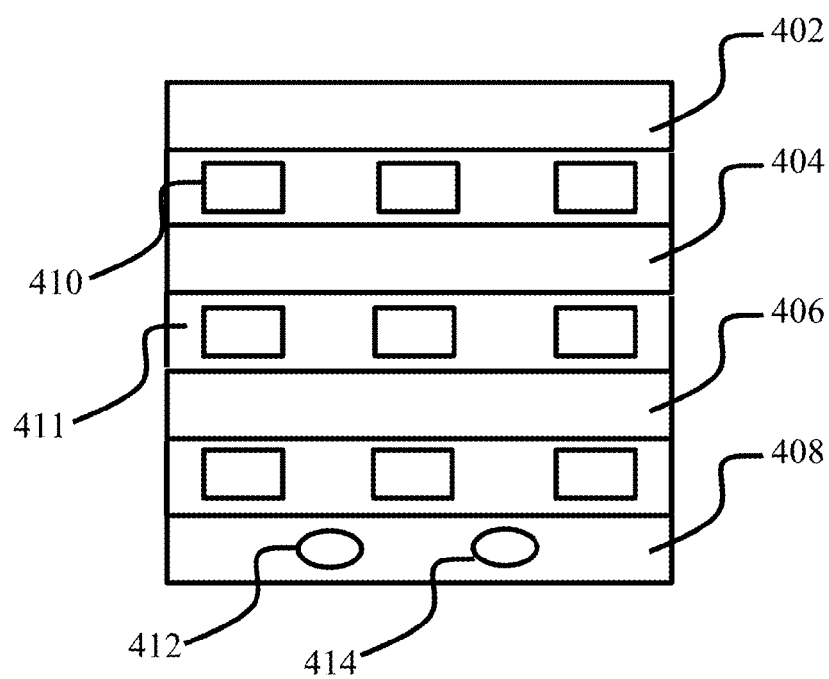
FIG. 4 is a front-view schematic of stackable retainers with sample materials for monitoring.

Referring now to FIG. 4, a front-view schematic of stackable retainers with sample materials for monitoring is provided. In monitoring vessel 400, stackable retainers 402, 404, 406, and 408 hold sample materials 410 in layers between the stackable retainers. Monitoring vessel 400 includes a temperature sensor 412 and a pressure sensor 414 for monitoring, transmitting, and recording pressure and temperature during the time period during which sample materials 410 are exposed to a fluid flowing in between stackable retainers 402, 404, 406, and 408. More or fewer pressure and temperature sensors can be used in other embodiments, and can be placed anywhere suitable for measuring the pressure and temperature, and/or other parameters such as flow rate, in the environment relevant to the sample materials.

Figure 5:
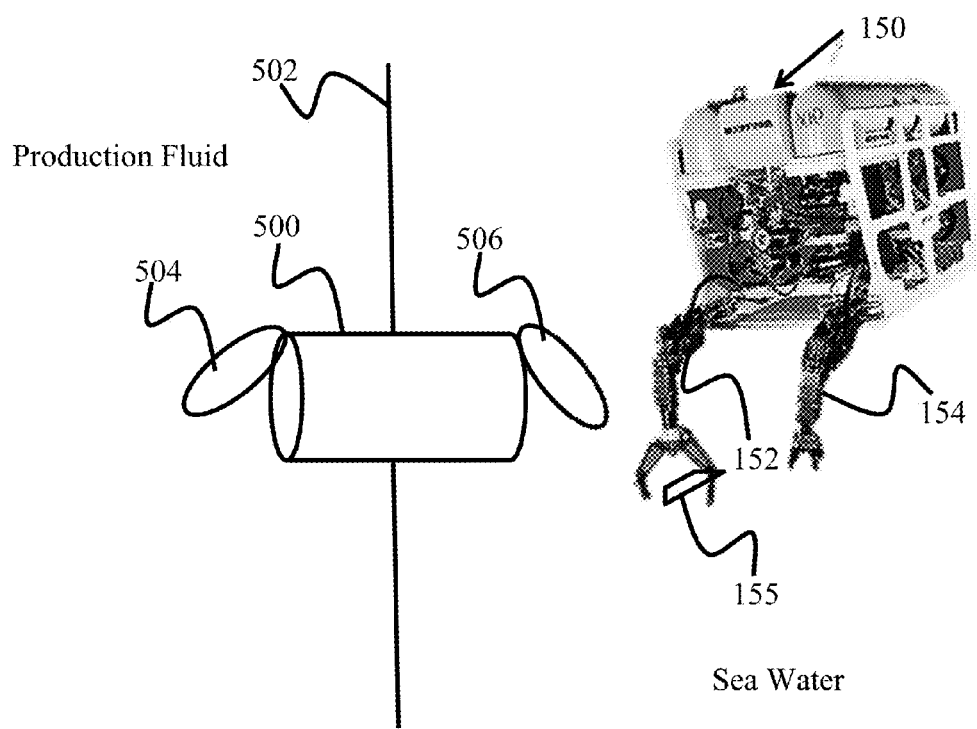
FIG. 5 provides a schematic for insertion of a sample material into a monitoring vessel.

Referring now to FIG. 5, a schematic for insertion of a sample material into a monitoring vessel is provided. Monitoring vessel 500 is disposed within a production line wall 502 with end caps 504 and 506. Material sample 155 can be placed in monitoring vessel 500 by ROV 150 while end cap 506 is open and end cap 504 is closed. Once the material sample 155 is placed in monitoring vessel 500, end cap 506 can be closed, and end cap 504 can be opened. In this way, the material sample 155 is exposed to production fluid. End caps 504, 506 can be opened and closed, in some embodiments, by an ROV, or can be controlled remotely by a user at the surface with either wireless or wired connections.

In some embodiments, monitoring vessels are not ROV retrievable and would be mounted on or in BOP equipment, and when an LMRP and/or lower stack is retrieved to surface, then the samples could be removed and sent in for testing.

Figure 6:
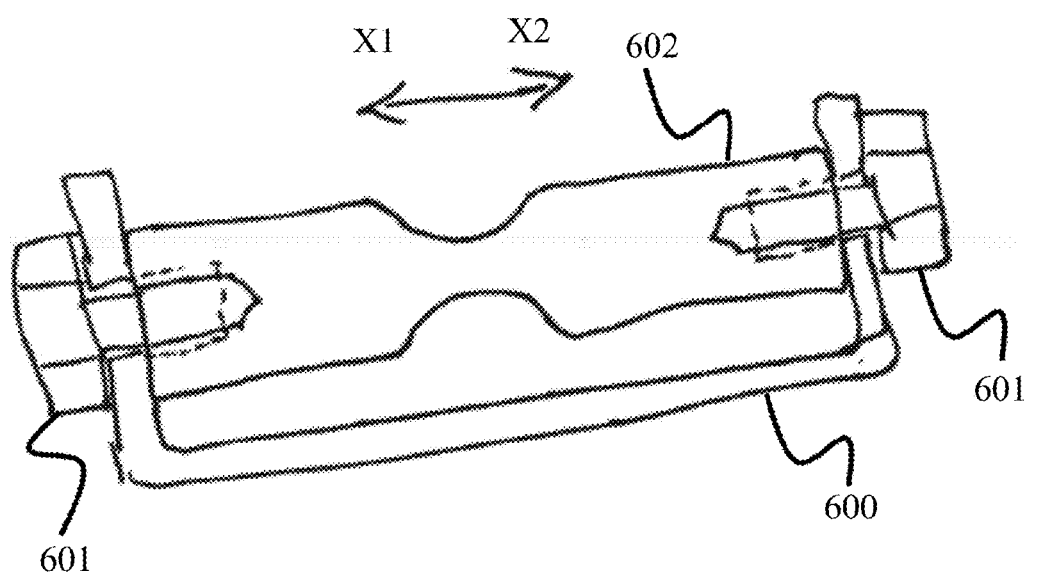
FIG. 6 provides a schematic of a sample material installed in a stackable retainer, such as that shown in FIG. 4, that is preloaded under tension.

Referring now to FIG. 6, a schematic of a sample material installed in a stackable retainer, such as that shown in FIG. 4, that is preloaded under tension is provided. A tension bar 600 provides tension outwardly in the X1 and X2 directions on a material sample 602. Such tension can also be referred to as a "preload" of tension. Tension bar 600 holds material sample 602 by grips 601. Some environmental conditions can reduce the ability of a material to handle stress levels, which results in environmental stress corrosion and cracking in tension loads. Such degradation is difficult to replicate in a lab environment. Samples can be preloaded to a varying number of tension loads, and if failure occurs, the strength levels can be correlated to the reduction in material strength while in the environment, and compared to the design limitations and fatigue life of the equipment. Such degradation testing over time while a material sample is under tension can be performed on both metallic and elastomeric materials.

The singular forms "a," "an," and "the" include plural referents, unless the context clearly dictates otherwise.

In the drawings and specification, there have been disclosed embodiments of methods and systems for condition-based monitoring for materials in wellbore applications, and although specific terms are employed, the terms are used in a descriptive sense only and not for purposes of limitation. The embodiments of methods and systems have been described in considerable detail with specific reference to these illustrated embodiments. It will be apparent, however, that various modifications and changes can be made within the spirit and scope of the embodiments of the present disclosure as described in the foregoing specification, and such modifications and changes are to be considered equivalents and part of this disclosure.

What is claimed is:

1. A method for analyzing material wear in a hydrocarbon production environment, the method comprising the steps of:
    preparing a sample of material to be disposed proximate the hydrocarbon production environment;
    selecting a placement location for the sample of material, wherein the placement location is in fluid communication with a fluid flow for which impact of the fluid flow on the sample of material is to be tested;
    placing the sample of material in a monitoring vessel with openings for the fluid flow;
    applying a preload of tension to the sample of material within the monitoring vessel to correlate strength reductions in the sample of material due to the hydrocarbon production environment;
    disposing the monitoring vessel in the placement location for a pre-determined amount of time;
    retrieving the sample of material from the placement location after the pre-determined amount of time has passed; and
    analyzing the sample of material for wear caused by the hydrocarbon production environment.

2. The method according to claim 1, wherein the method further comprises the step of monitoring temperature and pressure proximate the sample of material when the sample of material is exposed to the fluid flow.

3. The method according to claim 1, wherein the sample of material is selected from the group consisting of: a metallic material and an elastomeric material.

4. The method according to claim 1, wherein the placement location for the sample of material is proximate a blowout preventer (BOP) stack.

5. The method according to claim 1, wherein the placement location for the sample of material is an unused side outlet on a BOP stack.

6. The method according to claim 1, wherein the predetermined amount of time is about 1 year.

7. The method according to claim 1, wherein the fluid flow is selected from the group consisting of: production fluid flow and seawater flow.

8. The method according to claim 1, wherein the steps of disposing the sample of material and retrieving the sample of material are performed using a remotely operated vehicle (ROV).

9. The method according to claim 1, wherein the step of analyzing the sample of material for wear caused by the hydrocarbon production environment comprises destructive testing of the sample of material.

10. The method according to claim 1, further comprising the step of applying a cathodic connection to the placement location when the sample of material comprises a metal.

11. The method according to claim 1, further comprising:
  determining the preload of the tension at which the sample of material failed; and
  correlating strength reductions of the sample of material due to environmentally assisted stress corrosion cracking.

* * * * *